United States Patent [19]

Duranleau et al.

[11] Patent Number: 4,463,192

[45] Date of Patent: Jul. 31, 1984

[54] PROCESS FOR THE REDUCTION OF AN N-HYDROCARBYL SUBSTITUTED OXAZOLIDINE WITH CARBON MONOXIDE TO FORM THE CORRESPONDING N-HYDROCARBYL SUBSTITUTED ALKANOLAMINE

[75] Inventors: Roger G. Duranleau, Georgetown; Kenneth G. McDaniel, Round Rock, both of Tex.

[73] Assignee: Texaco Inc., White Plains, N.Y.

[21] Appl. No.: 510,789

[22] Filed: Jul. 5, 1983

[51] Int. Cl.³ .............................................. C07C 85/00
[52] U.S. Cl. ..................................... 564/467; 564/487
[58] Field of Search ........................................ 564/467

[56] References Cited

U.S. PATENT DOCUMENTS 4,024,184  5/1977  Kaiser et al. ..................... 564/487 X
4,138,468  2/1979  Kettner et al. ................... 564/487 X
4,281,200  7/1981  Snoble ................................. 564/487

Primary Examiner—Paul F. Shaver
Attorney, Agent, or Firm—Robert A. Kulason; Kenneth R. Priem; James J. O'Loughlin

[57] ABSTRACT

A process for the preparation of N-hydrocarbyl substituted alkanolamines which comprises reacting a specified oxazolidine with carbon monoxide at a temperature ranging from 50° to 250° C. and a pressure ranging from 100 to 2500 psig, said oxazolidine being represented by the formula:

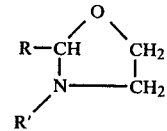

in which R is an alkyl radical of 1 to 3 carbon atoms and R' is an alkyl radical of 1 to 10 carbon atoms or a hydroxy alkyl radical of 1 to 10 carbon atoms.

6 Claims, No Drawings

PROCESS FOR THE REDUCTION OF AN N-HYDROCARBYL SUBSTITUTED OXAZOLIDINE WITH CARBON MONOXIDE TO FORM THE CORRESPONDING N-HYDROCARBYL SUBSTITUTED ALKANOLAMINE

FIELD OF THE INVENTION

In recent years, there has been a great increase in the number of applications discovered for N-hydrocarbyl substituted alkanolamines; for example, they are being used as anti-rust compounds, emulsifiers for polish, textile chemicals, corrosion inhibitors, pharmaceutical intermediates, agricultural chemicals, and emulsifying agents. Correspondingly, the manufacturing output requirement for N-hydrocarbyl substituted akanolamines, such as methyldiethanolamine, have also increased.

The processes for preparing N-hydrocarbyl substituted alkanolamines employed heretofore have been deficient in a number of respects, including cost, efficiency, and safety in manufacture. In one process of manufacture, an alkyl halide is reacted with an alkanolamine to form N-alkyl derivatives. In another process, an oxazolidine ring is reduced with formic acid to form the N-hydrocarbyl substituted alkanolamine.

It is an object of the instant invention to overcome these deficiencies by eliminating the need both for a halide alkylating agent and for formic acid in the preparation of N-hydrocarbyl substituted alkanolamines.

DISCLOSURE INFORMATION STATEMENT

Kirk Othmer, *Encyclopedia of Chemical Technology* (Second Edition, Vol. 1) at page 813 discloses reacting an alkanolamine with an alkyl halide to form N-alkyl derivatives.

Kirk-Othmer, *Encyclopedia of Chemical Technology* (Third Edition, Vol. 11) at pages 259 and 264 to 265, discloses carbonylation reactions with ammonia and amines wherein ammonia or an amine are reacted with carbon monoxide in the presence of a solvent containing a basic catalyst, for example, sodium methoxide in methanol, at temperatures ranging from 80° to 200° C. and at pressures ranging from 400 to 1500 psig to produce the corresponding formamide or dimethylformamide.

An article in Chemical Abstracts (47:9724-5) discloses the absorption of carbon monoxide by a solution containing cuprous monoethanolamine complex.

Swedish Patent Nos. 132,874 and 132,772 (CA 46, 6670 and CA 46 6671, respectively) disclose the reduction of oxazolidine with formic acid.

SUMMARY OF THE INVENTION

Provided is a process for preparing N-hydrocarbyl substituted alkanolamines which comprises reacting a specified oxazolidine with carbon monoxide at a temperature ranging from 50° to 250° C. and a pressure ranging from 100 to 2500 psig, said oxazolidine being represented by the formula:

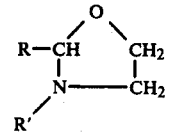

in which R is an alkyl radical of 1 to 3 carbon atoms and R' is an alkyl radical of 1 to 10 carbon atoms or a hydroxy alkyl radical of 1 to 10 carbon atoms.

DETAILED DESCRIPTION OF THE INVENTION

In the process of the instant invention, the prescribed oxazolidine is subjected to a temperature ranging from 50° to 250° C. in the presence of carbon monoxide at a pressure ranging from 100 to 2500 psig. Preferably, the temperature employed ranges from 100° to 175° C. and the pressure employed ranges from 500 to 1500 psig, and most preferably the temperature employed ranges from 125° to 160° C. and the pressure employed ranges from 750 to 1300 psig.

The oxazolidine employed in the instant invention is represented by the formula:

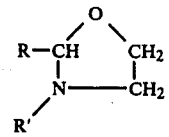

in which R is an alkyl radical of 1 to 3 carbons and R' is an alkyl radical of 1 to 10 carbon atoms or a hydroxy radical of 1 to 10 carbon atoms. Suitable R groups include methyl, ethyl, propyl and isopropyl. Suitable R' groups include ethyl, methyl, isopropyl, pentyl, and the like, or 2-hydroxy ethyl, 3-hydroxy propyl, 1-hydroxy propyl, 1-hydroxy butyl, 2-hydroxy butyl, 2-hydroxy pentyl, and the like. The preferred oxazolidine is N-(2-hydroxyethyl) oxazolidine.

Utilizing the process of the instant invention, the prescribed oxazolidine is charged to a reaction vessel and subjected to temperatures ranging from 50° to 250° C. and to carbon monoxide at a pressure ranging from 100 to 2500 psig. At these temperatures and pressures, the carbon monoxide present in the reactor successfully reduces the oxazolidine compound, and it was found that the reaction process is not dependent on the presence of water in the reactor, that is, good yields of product were obtained both when the reaction was run in the presence and absence of water.

As a end result of the instant process, the oxazolidine is reduced to the corresponding N-hydrocarbyl substituted alkanolamine. In case where, for example, the oxazolidine is N-(2-hydroxyethyl) oxazolidine, the N-hydrocarbyl substituted alkanolamine formed is methyl diethanolamine. In like manner, N-ethyl oxazolidine forms N-substituted methyl, ethyl, ethanolamine; and N-methyl oxazolidine forms N-dimethylalkanolamine. In this way, by properly choosing the oxazolidine reactant, the desired N-hydrocarbyl substituted alkanolamine can be formed.

The nature of this invention and the manner in which it is practiced will be better understood when reference is made to the following examples which include preferred embodiments. These examples, however, are not meant in any way to limit the scope of the invention.

EXAMPLE 1

58.5 grams (0.5 mole) of N-(2-hydroxyethyl) oxazolidine and 10 grams (0.555 mole) of water were charged to an autoclave. The autoclave was then flushed with carbon monoxide, sealed, and heated to 150° C. Thereafter, the carbon monoxide pressure was increased to 830 psig. After 9 hours the autoclave was cooled and vented. The 68.5 grams of product was found by gas chromatographic and NMR analysis to consist of a mixture of diethanolamine (34%) and methyldiethanolamine (34.3%) and a small percentage of unknowns. The hydroxyethyl oxazolidine was completely consumed.

EXAMPLE 2

Reaction process without the presence of water 58.5 grams (0.5 mole) of N-(2-hydroxyethyl) oxazolidine was charged to an autoclave which had been carefully pre-dried to remove any traces of water. After charging, the carbon monoxide pressure was raised to 300 psig and the temperature was increased to 140° C. The pressure was then elevated to 1200 psig by the further addition of carbon monoxide. After 4 hours, the autoclave was cooled and, after venting, the liquid products collected. The 57 grams of product were analyzed by gas chromatography and NMR spectroscopy and found to be a mixture of diethanolamine (27.3%) and methyldiethanolamine (40.8%) and unreacted starting material (9%).

EXAMPLE 3

The same procedure as outlined in Example 1 was repeated, except that 9.0 grams (0.5 moles) of water was employed and the pressure was maintained at 1250 psig for 4 hours. The 63.4 grams of product were analyzed by gas chromatography and NMR spectroscopy and found to contain diethanolamine (19.9%) N-methyldiethanolamine (46%) and a trace of starting material.

The foregoing examples illustrate the effectiveness of this novel process for reacting an N-hydrocarbyl substituted oxazolidene with carbon monoxide to produce a substantial yield of the corresponding N-hydrocarbyl alkanolamine.

We claim:

1. A process for preparing an N-hydrocarbyl substituted alkanolamine which comprises subjecting an N-hydrocarbyl substituted oxazolidine to a reaction with carbon monoxide at a temperature ranging from 50° to 250° C. and a pressure ranging from 100 to 2500 psig, said oxazolidine being represented by the formula:

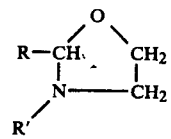

in which R is an alkyl radical of 1 to 3 carbon atoms and R' is an alkyl radical of 1 to 10 carbon atoms or a hydroxy alkyl radical of 1 to 10 carbon atoms.

2. A process according to claim 1 wherein the temperature employed ranges from 100° to 175° C. and the pressure employed ranges from 500 to 1500 psig.

3. A process according to claim 2 wherein the temperature employed range from 125° to 160° C. and the pressure employed ranges from 750 to 1300 psig.

4. A process according to claim 1 wherein the oxazolidine is N-2-(hydroxyethyl) oxazolidine.

5. A process according to claim 1 wherein water is present during the course of the reaction.

6. A process for preparing methyldiethanolamine which comprises subjecting a N-(2-(hydroxyethyl) oxazolidine to a temperature ranging from 125° to 160° C. and to carbon monoxide at a pressure ranging from 750 to 1300 psig.

* * * * *